United States Patent [19]
Birkholz et al.

[11] Patent Number: 5,480,610
[45] Date of Patent: Jan. 2, 1996

[54] PROCESS AND APPARATUS FOR THE DISINFECTION OF WASTE

[75] Inventors: Michaela Birkholz; Stefan Drauscke; Gerhard Hörber, all of Berlin, Germany

[73] Assignee: Krankenhausentsorgungsellschaft mbH, Berlin, Germany

[21] Appl. No.: 15,197

[22] Filed: Feb. 11, 1993

[30] Foreign Application Priority Data

Feb. 14, 1992 [DE] Germany ................. 42 04 444.8

[51] Int. Cl.⁶ .................. A61L 2/06; A61L 2/26
[52] U.S. Cl. ........................ 422/26; 422/295
[58] Field of Search ............... 422/26, 32, 33, 422/38, 295, 307, 171, 298

[56] References Cited

U.S. PATENT DOCUMENTS

| | | | |
|---|---|---|---|
| 4,108,601 | 8/1978 | Wolff | 422/295 |
| 4,166,096 | 8/1979 | Gillis et al. | 422/119 |
| 4,284,600 | 8/1981 | Gillis et al. | 422/26 |
| 4,296,067 | 10/1981 | Näsman et al. | 422/26 |
| 4,670,223 | 6/1987 | Delachapelle | 422/171 X |
| 4,685,507 | 8/1987 | Schäfer | 422/26 X |
| 4,808,377 | 2/1989 | Childers et al. | 422/298 X |
| 4,999,167 | 3/1991 | Skelley et al. | 422/172 X |
| 5,132,084 | 7/1992 | Harrell et al. | 422/26 |
| 5,223,229 | 6/1993 | Brucker | 422/298 X |

FOREIGN PATENT DOCUMENTS

| | | |
|---|---|---|
| 0031790 | 7/1981 | European Pat. Off. |
| 0454122 | 10/1991 | European Pat. Off. |
| 3039173 | 4/1982 | Germany |
| 3444197 | 6/1985 | Germany |
| 3913472 | 10/1990 | Germany |
| 4014856 | 11/1991 | Germany |

Primary Examiner—Robert J. Warden
Assistant Examiner—E. Leigh Dawson
Attorney, Agent, or Firm—Nies, Kurz, Bergert & Tamburro

[57] ABSTRACT

A process and apparatus for disinfection of waste in autoclaves by the fractional vacuum-steam process having atmospheric pressure steam phases, followed by a superatmospheric steam phase and a evacuation of the autoclave following each steam phase. The autoclaves are transportable separate from the remaining apparatus. In the evacuation after an atmospheric pressure steam phase, removing the atmosphere from the autoclave by suction, condensing the steam fraction and separating it as liquid having approximately ambient temperature. During evacuation after a superatmospheric pressure steam phase, first eliminating condensate from the lowest part of the autoclave, and feeding it to waste water at approximately ambient temperature. Evacuation following an atmospheric pressure steam phase is from an upper region of the autoclave, the atmosphere being then freed from micro-organisms. The steam is removed and gas fractions are freed from odorous substances and discharged to the environment. Evacuation after the superatmospheric pressure steam phase, after eliminating the condensate from the lowest point of the autoclave, is by removing the atmosphere by suction from the lower or upper region of the autoclave and freeing it from odorous substances prior to discharge into the environment. The device for eliminating the micro-organisms on charging the autoclave with process steam being connected to the autoclave and the atmosphere is removed from the autoclave by suction and freed from micro-organisms and solids by using filters.

30 Claims, 2 Drawing Sheets

PROCESS AND APPARATUS FOR THE DISINFECTION OF WASTE

DESCRIPTION

In industry and, especially, also in hospitals, infectious contaminated materials are produced, for the disposal of which the legislator specifies high requirements.

In the case of hospitals wastes, a distinction is made in this context between "wet" wastes such as blood and organ parts etc., and so-called "dry" wastes such as used dressings, paper sheets, swabs etc.

If these materials, for safety reasons, are individually disinfected or sterilized by each hospital on site, this causes very high costs, since the plant necessary therefor cannot generally be used to capacity by the corresponding waste from only one hospital.

The invention therefore relates to a process and an apparatus for carrying out this process for disposing of such infectious, dry wastes, without the devices necessary therefor having to be provided at each user hospital.

In principle, these dry wastes are collected in the hospitals in special waste sacks and are deposited in closeable central containers. The disinfection or sterilization is carried out in a manner known per se in pressure-tight autoclaves which can be charged with steam by the so-called fractional vacuum steam process.

In this process, the container filled with the infected material is filled a plurality of times on each occasion with steam and is then evacuated as far as possible. In a last step, the autoclave is charged with saturated steam at superatmospheric pressure and this state is maintained at a steam temperature of approximately 110° C. for about 15 minutes, as a result of which the content of the autoclave is disinfected. At a holding temperature of 134° C. of the saturated steam, moreover, sterilization takes place. The special waste sacks, which, together with their infectious contents, are thrown without being reopened into the autoclave, are permeable to steam, so that the entire contents of the autoclave experiences disinfection or sterilization.

In order to make possible the abovementioned disposal without the necessary buildings for individual hospitals, it is already disclosed by German Offenlegungsschrift 3,039,173 to use mobile autoclaves mounted on a truck which are located with the respective wastes at the hospital and are driven to a stationary disposal site, where the autoclave, via appropriate connections, can be filled with process steam and also heated via its jacket space and, via suction connections, the atmosphere of the autoclave can be removed by suction.

It is a disadvantage in this case that these disposal sites, because of the relatively high expense in terms of construction, cannot be provided as often as is desired, so that the autoclave vehicles have long journeys to make between hospitals and disposal site, which not only increases the costs, but also the risk of accident, despite the secure construction of the autoclaves.

In addition, the problem of the disinfection of the atmosphere of the autoclave removed by suction in the first evacuation steps has hitherto demand too high an expenditure and likewise the problem or odor pollution, which, in addition to the technical requirements of such disposal sites, was accompanied by a further restriction on the selection of location for such disposal sites.

It is thus the object of the present invention to create a process for the disposal of infectious waste and an apparatus for carrying this out which is unproblemmatic with regard to disinfection and odor neutralization of the exhaust vapors and makes possible a variable use, with regard to location, of this type of disposal.

This object is achieved by the distinguishing features of claims 1, 3 and 9. Advantageous embodiments are given by sub-claims.

According to the invention, the process for disinfection using a fractionated vacuum-steam process is developed to the effect that in the evacuation following the atmospheric pressure steam phase, the steam vapors which are contaminated are first freed from all substances which are equal size to, or larger than, a virus, a bacteria or another microorganism. This purification is carried out with the aid of a plurality of filters, preferably two, connected in series having decreasing pass size, the finer having a pass size of 0.2 μm, so that even microorganisms are retained in this so-called sterile filter. Such a fine sterile filter would, obviously, be immediately plugged by steam droplets, since some of the steam contained would be condensed on passing through the filter and the water droplets formed during this would immediately plug the pores of the sterile filter. The prefilter of about 1.2 μm connected upstream of the sterile filter is therefore fine enough to retain steam droplets. The condensate produced at the filters, after disinfection, is separately discharged into the waste water.

The filters can be cleaned using process steam which is not contaminated. For this purpose, the coarser prefilter is charged against the normal direction of flow, as a result of which the particles collected in it are forced back out into the sump of the prefilter. The sterile filter and also the prefilter can be charged by process steam in the direction of flow and, after an appropriate holding time, be disinfected by the action of process steam. It is to be assumed in this case that microorganisms scarcely reach the sterile filter, since the microorganisms are generally taken up by the very fine water droplets contained in the exhaust air and are thus already retained in the prefilter together with these water droplet.

For this purpose, any valves arranged between the autoclave and the filters are opened and the valves arranged downstream of the filters in the direction of flow are closed, while the interior of the autoclave is charged with steam. As a result, the contents of the filter and the filter sump, together with the contents of the autoclave, are also sterilized or disinfected during the subsequent superatmospheric pressure steam phase.

For removal of the non-regenerable sterile filter, prior to removal, this is once more charged with process steam for safety, by passing process steam directly to the filters using a bypass pipe and the surrounding valves are closed.

After passing through the filters, the—now aseptic— exhaust vapors are conducted via a condenser to condense as high as possible a fraction of the steam contained and to feed the condensate likewise to the waste water. The substantially dry exhaust air is discharged to the ambient air via a unit for odor neutralization.

A different treatment is applied to the exhaust vapors which are removed by suction in the evacuation of the autoclave following the superatmospheric pressure steam phase: from the lowest point of the interior of the autoclave, the condensate collected there is pumped off, after let off of the pressure of the interior of a point in the upper part, and the gaseous constituents always contained are separated off for example, by the help of cyclone and, after odor neutralization, are discharged to the ambient air. The liquid constituents, after cooling to approximately ambient temperature, are fed to the waste water.

After the condensate has been pumped off, the essentially gaseous atmosphere is removed from the autoclave either by continuing to remove it by suction from this lowest point after the condensate has been disposed of, or, in a further procedure, removing the atmosphere from the autoclave by suction from a higher exhaust point.

In any case, these exhaust vapors are passed via a condenser and after the liquid fraction and gas fraction are separated, are fed to the waste water or to the ambient air. In addition, the exhaust vapors can be passed over filters, in order primarily to filter out solids which could damage the vacuum pumps.

In order not to let the temperature in the autoclave drop during the holding time in the superatmospheric pressure steam phase, the autoclave is jacketed in a known manner and is likewise charged with process steam in the jacket space surrounding the interior. The process steam is kept saturated by temporarily storing the condensate produced in the feed lines for the process steam and in the jacket space of the autoclave in a condensate receiver and returning it to the process steam via a corresponding pump. In the event that an insufficient amount of condensate is present, the saturation can also be carried out using fresh water.

The odor neutralization of the exhaust vapors is carried out by first passing the gases through a zone of very fine mist, for example produced by ultrasonic jets, composed of a washing liquid, in which the odor substances are taken up by the mist droplets. In a subsequent separating layer composed of a solid having a high specific surface area, such as lava rock or tuff, through which the gases are conducted in countercurrent to the circulation liquid sprayed onto the separation layer, the separation of the liquid droplets loaded with odorous substances from the gases to be discharged is carried out. The droplets not yet retained are subsequently retained in a conventional demister. The washing liquid in this case is circulated and is thus subjected to an increasing contamination, uncontaminated washing liquid only being used in the generation of the very fine mist.

The water-based washing liquid is subsequently used as a circulation liquid and can contain solubilizers in order to wash out the sparingly water-soluble air contents, such as essential oils and, possibly, additional substances which enter into a chemical reaction with the odor-intensive air contents, as a result of which a deodorizing effect takes place. For example, oxidizing agents such as hydrogen peroxide are considered for this.

The odor neutralization can alternatively be undertaken using an adsorption filter, by passing the exhaust vapors over, for example, dry activated charcoal.

The autoclave designed to be portable is provided in this case, in addition to the actual, jacketed autoclave only the connections for the steam charging of the interior and of the jacket space, and a discharge connection for the condensate formed in the jacket space and at least one exhaust connection for the atmosphere in the interior of the autoclave.

All other units, pipes and valves such as filters, condenser, liquid separator, gas scrubber, condensate receiver and control unit required for the above described process are accommodated in a so-called power unit, which can likewise be designed to be mobile by accommodating it in an easily transportable standard container. This power unit will in turn generally have external connections, chiefly for process steam and electrical energy, since, depending on the opportunity, steam from surplus capacities of thermal power stations etc., will be used instead of the significantly more expensive generation of process steam from primary energy.

However, the relatively mobile design of the power unit provides the opportunity to transport this power unit at relatively long intervals of time from one suitable installation site to another and thus greatly to reduce the journey lengths of the mobile autoclaves.

In addition, the power unit contains a fresh water connection for saturation of the process steam and dilution of the circulation liquid in the gas scrubber. In order to keep the capacity of the necessary fresh water connection small, both the condenser and any additional cooling devices at the liquid separators, with the aid of which the liquid constituents are cooled down to approximately ambient temperature, in order to permit them to be supplied to the normal waste water, are air-cooled. For the purpose of this cooling, preferably, two separate liquid separators are available which can be charged alternately, in order while one liquid separator is being charged, to be able to cool the other to the desired waste water temperature. The same purpose is fulfilled by a single, appropriately large-dimensioned liquid separator.

These liquid separators are preferably designed as cyclones, in order to achieve as complete as possible a liquid separation. Otherwise, a part of the condensate would be re-evaporated by the subsequently arranged vacuum pumps and would be fed via the moisture-sensitive vacuum pumps additionally to the gas scrubber, which would lead to a marked increase and dilution of the washing liquid. The circulation liquid essentially circulated in the gas scrubber, on attaining its maximum pollutant load, is likewise wholly or partially fed to the waste water discharge line of the power unit.

A bypass line containing process steam surrounding the autoclave opens in the discharge line between the prefilter and the sterile filter in order to offer the previously described possibility of cleaning these filters. In addition to the exhaust connection arranged relatively high in the autoclave interior, the autoclave can also be provided with an exhaust connection arranged at the lowest point of the interior, which preferably opens in the exhaust line available upstream of the condenser but downstream of the filters, but by means of a branch can also be diverted to an opening upstream of the condenser and the filters.

The power unit further contains a pump, arranged between the condensate receiver and the process steam feed, and a corresponding return line, with the aid of which the condensate produced in the feed lines of the process steam and in the jacket space is returned to the process steam to saturate it, if necessary with the addition of fresh water if the amount is insufficient.

The connections between autoclave and power unit are preferably formed as ball valves, since this type of construction best enables a disinfection of the contact surfaces of the valves by the superatmospheric steam phase in the autoclave.

An embodiment according to the invention is described in more detail below as an example on the basis of the figures.

In the diagrams:

FIG. 1 shows the autoclave 25, whose constituents are surrounded by a dashed line:

Figure 1:
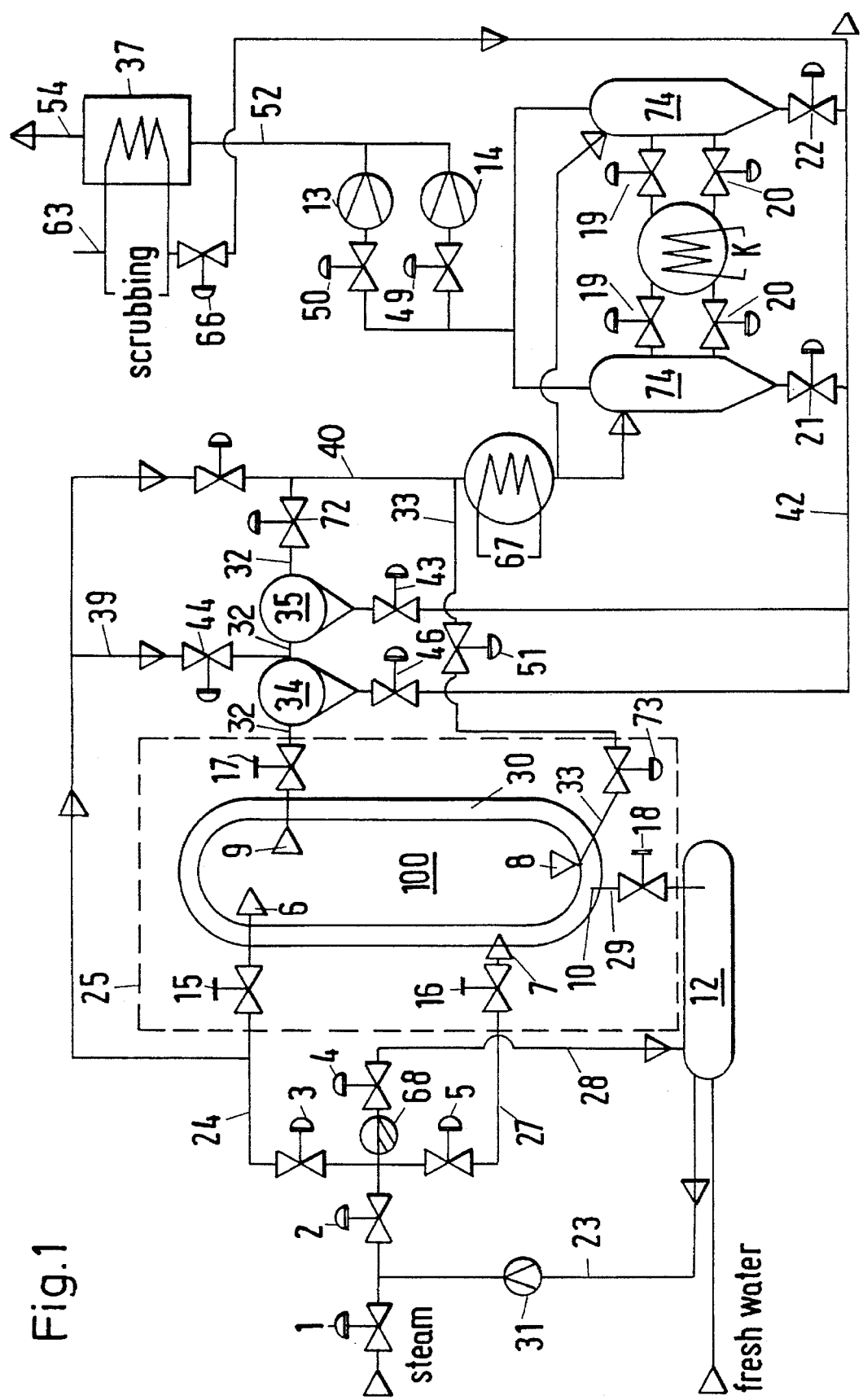
FIG. 1 shows a diagram of the principle of the autoclave connected to the power unit and FIG. 2 shows a cross-sectional diagram of the gas scrubber.

The interior 100 of the autoclave is surrounded by a jacket, which forms the surrounding jacket space 30. The steam connection 6 for the entry of the process steam opens in the interior, as does a high exhaust connection 9 for removing the interior atmosphere by suction as does a low exhaust connection 8 at the lowest point of the autoclave interior, from which the condensate collected there can be removed by suction.

The feed line 24 to the steam connection 6 and the exhaust lines 32 and 33, which lead away from the exhaust connections 8 and 9 of the interior, can each be shut off by coupling valves 15, 17 and 73 and are detachable from the surrounds, which thus represent the interface of the autoclave with the surrounds.

Likewise, the feed line 27 opening in the steam connection 7 of the jacket space 30 is also closeable by such a coupling valve 16 and is designed to be separable, as is the condensate connection 10 leading from the lowest point of the jacket space 30, the discharge line 29 of which is likewise provided with such a coupling valve 18.

All the elements depicted outside the dashed line and thus the transportable autoclave 25 are located in a unit termed the power unit, which is accommodated in a mobile container and as a result although this is moved less often than the autoclave itself to another location, since this would damage in the long term the, in some cases, highly sensitive units, nevertheless permits a change of location at longer intervals of time.

This power unit itself must be supplied with process steam for charging the autoclave—for which, preferably, surplus capacities etc., are used at suitable locations—and with electrical power for the supply of the control unit and the multiplicity of control valves and with fresh water for the saturation of the process steam and to dilute the washing fluid of the gas scrubber 37.

The residues from the evacuation of the autoclave leave the power unit in gaseous form via the outlet line 54 of the gas scrubber 37 and in aqueous form via the waste water line 42 which opens into the waste water system available on site. The feed of process steam into the power unit is regulated via valves 1 and 2. The intermittent introduction of process steam necessary according to the fractional vacuum-steam process via the feed line 24 into the interior 10 is regulated via a further valve 3, while valve 5 controls the introduction of process steam via the feed line 27 into the jacket space 30 which is usually almost continuously heated in order to prevent too heavy a condensation of the process steam introduced into the interior 100 on the cold outer surface of the autoclave.

The condensate from process steam produced in the feed lines is trapped in a receiver 68 and can be discharged from there by means of a valve 4 into the central condensate receiver 12 via a line 28. The process steam condensate collected in the jacket space 30 is also discharged into the condensate receiver 12 from the condensate connection 10 via the coupling valve 18 as required.

The contents of the condensate receiver 12, which, if necessary, can be replenished via a fresh water connection, is returned via a return line 23 and a pump 31 to the process steam feed between the valves 1 and 2 to saturate the process steam with water.

The atmosphere of the interior 100 of the autoclave charged with process steam is removed by suction after each cycle via the exhaust connections 8 or 9 and—separated into liquid and gaseous fractions and according to specific subsequent treatment—returned to the surrounds.

In order to ensure that the substances returned to the surrounds from the autoclave are aseptic, a prefilter 34 and a sterile filter 35 are arranged in the exhaust line 32 leading from the high exhaust connection 9 downstream of the coupling valve 17 and further along a shut-off valve 72. A line 39 opening directly between the filters 34 and 35, via which clean process steam can be fed, can also be shut off via a valve 44. The same also applies to the discharge lines, via which the sump of the filter 34 and 35 is connected to the waste water line 42. These can also be shut off tight via valves 46, 43.

When the interior 100 of the autoclave is charged with process steam, these two filters are also charged by keeping open the coupling valve 17 arranged between the filters and the autoclave, but keeping closed the valves 46, 43, 44 and 72 surrounding the filters. Although these filters are arranged in the power unit, they are part of the region impinged by steam. As a result, substances retained in the filters 34, 35 are disinfected. The residues collecting as a liquid in the filter sump can thus, as required, after disinfection has been carried out, be discharged via the valves 46, 43 without problem to the waste water line 42.

The prefilter 34 has a pass size of 1.2 μm and serves to retain such solids and liquid droplets which would immediately plug the subsequent sterile filter 35.

The prefilter 34 can be backwashed via process steam supplied in the opposite direction from line 39 which opens to line 32 between prefilter and sterile filter 35.

When the coupling valve 17 is closed, the substances located in this case in the prefilter 34 are flushed into the sump of the prefilter 34 and thus pass into the waste water line 42. In contrast to the prefilter 34, the sterile filter 35 cannot be regenerated after binding. However, by charging via the line 39 with process steam when the surrounding valves are closed, the filter cake of the only 0.2 μm fine sterile filter 35, which also retains microorganisms such as bacteria and viruses, can be treated with sufficiently long holding time and sufficient pressure, for safety—just as the prefilter 34 and its filter sump—until a disinfection or sterilization have been achieved, before the filter cake of the sterile filter 35 is disposed of and the filter sump of both filters is discharged in each case into the waste water line 42.

The atmosphere removed by suction from the interior 100 by vacuum pumps 13, 14 connected in parallel is fed, from interior 100, in further progression via a line 32, 40 to a condenser. 67 in order to achieve as complete as possible a condensation of the steam contained in the exhaust vapors. The condensate formed in this and the remaining gaseous constituents are then alternately fed to one of two parallel liquid separators in the form of cyclones 74 in the shortest possible pathways, in which the liquid fraction is separated off and is fed via valves 21, 22 to the waste water line 42. This liquid separation by means of a cyclone is necessary in order that as a result of the suction action of the vacuum pumps 13, 14 arranged downstream of the liquid separators 74 and the condenser 67 a significant part of the condensate form is again evaporated.

In the liquid separation care should be taken that the introduction of the condensate into the waste water line 42 takes place at a temperature approximating that of the ambient temperature, that is about 20° C. Since the condensate produced in the condenser 67 is generally significantly warmer, the two liquid separators 74 are fed alternately, the contents of the liquid separators 74 not currently being fed being cooled down with the aid of a cooler K and corresponding valves 19, 20. In order that, in addition to the fresh water, still greater amounts of cooling water are not required for the power unit, the cooler K is cooled by ambient air.

The gaseous fractions separated off in the cyclones 74 are removed by suction via the vacuum pumps 13, 14—which can be individually switched on and shut off via line 52 and through the valves 49, 50—and discharged via a gas scrubber 37 to the ambient air.

In addition to the removal of the atmosphere by suction described via a high exhaust connection 9, a lowlying exhaust connection 8 is located in the interior 100 of the autoclave at the lowest point of the interior 100. The exhaust line 33 from this low exhaust connection 8, includes control valves 73 and line 51 and directly upstream of the condenser 67. When the condensate is first pumped off from this low connection 8 in the interior 100, it flows through the condenser 67 without effect.

The essentially gaseous vapors removed by suction from the same connection 8 must, in contrast, pass through this condenser 67 to condense.

Passing the vapors removed by suction from this low-lying connection 8 through the filters 39 and 35 is not necessary, since material is only removed by suction from the low-lying connection 8 after the subsequent superatmospheric steam phase which leads to disinfection or even sterilization of the contents of the autoclave.

Figure 2:
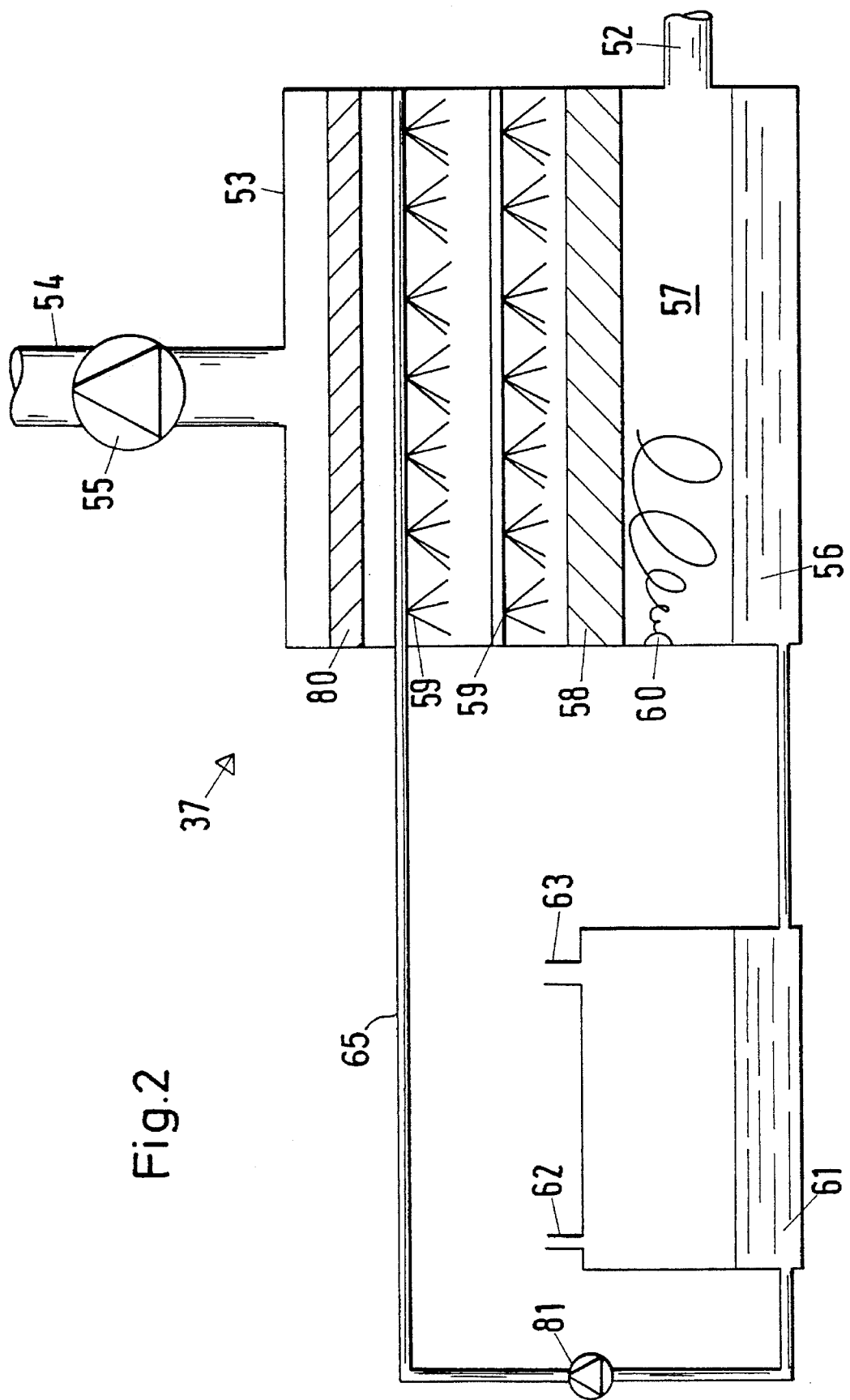

A circulation fluid essentially circulates in the gas scrubber 37, which is depicted in detail in FIG. 2, which circulation liquid, as the contamination increases, can be additionally diluted by fresh water and can be wholly or partly discharged via the valve 66 into the waste water line 42.

As is shown in detail in FIG. 2, the gas scrubber 37 is composed of a shell 53 in which the gases to be purified are passed essentially from bottom to top and thus pass through various layers in which the odor substance-carrying constituents are washed out of the gas by means of the circulation liquid which is essentially conducted in countercurrent.

For this purpose, an internal receiver 56 of circulation liquid is located on the base of the shell 53. The gas to be purified is introduced via the line 52 into the shell above the liquid surface of the internal receiver and ascends because of a suction pump 55 arranged in the outlet line 54 downstream of the gas scrubber 37. A mist region 57 is located above the internal receiver 56, in which mist region a very fine mist of unpolluted washing liquid is produced by means of ultrasonic spray jets 60, which washing liquid is then used as circulation liquid. The odorous substances of the gases to be cleaned are taken up by these mist droplets.

Above this is located a separating layer 58 composed of a solid having a high specific surface area such as lava rock or tuff, which, in addition, must be sufficiently gas-permeable. This separating layer 58 is additionally sprayed with circulation liquid from above by sprinklers 59, in order to improve the washing out of the odorous substances from the gases. A demister 80 known per se is located above the sprinklers 59, which demister is not wetted by circulation liquid and serves to retain as many liquid droplets as possible.

The circulation liquid fed in sprinklers 59 via a line 65 is taken from an external receiver 61 of the washing liquid, which acts as a buffer store and is fed via a pump 81 to the sprinklers 59. In addition to a fresh water connection 63 to dilute the circulation liquid, a discharge valve 66 is arranged in the external receiver 61 towards the waste water line 42, as is a vent connection 62.

The gases leaving this contact scrubber are freed from odor-intensive constituents to such an extent that no odor pollution occurs in the surroundings of the power unit.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. In a process for the disinfection of waste by a fractional vacuum-steam process with at least one of a plurality of atmospheric pressure steam phases and a final superatmospheric steam phase with an evacuation following any such steam phase in an autoclave, the autoclave having upper and lower regions, including providing a load of waste to be disinfected and an autoclave, loading the waste into the autoclave, introducing steam into the autoclave at atmospheric pressure a plurality of times, evacuating the autoclave after each steam introduction step, and charging the autoclave with saturated steam at superatmospheric pressure during a final steam introduction step and maintaining the steam pressure until the autoclave is disinfected, wherein the improvement comprises: in the evacuation following an atmospheric pressure steam phase, removing by suction the atmosphere from an upper region of the autoclave; eliminating micro-organisms from the removed atmosphere, wherein the elimination of the micro-organisms is effected by apparatus connected to the autoclave and subjected to the same conditions as the autoclave; condensing and separating the steam fraction from the remaining gaseous fraction as a liquid fraction having approximately ambient temperature, eliminating odorous substances from the gaseous fractions and discharging the gaseous fractions to the environment; in the evacuation following a superatmospheric pressure steam phase, eliminating, from the lower region of the autoclave, the condensate which is collected there and feeding it to waste water at approximately ambient temperature, and then removing the atmosphere in the autoclave by suction, from one of the lower region and upper region of the autoclave and eliminating from the atmosphere, so removed, the odorous substances prior to discharge of the atmosphere into the environment.

2. The process as claimed in claim 1, wherein, during the evacuation following the superatmospheric steam phase, after the condensate has been removed by suction, the atmosphere removed from the autoclave by suction is condensed prior to being freed from odorous substances.

3. A process according to claim 1, wherein the evacuation following the superatmospheric pressure steam phase, the atmosphere is freed from solids.

4. The process as claimed in claim 1, wherein the autoclave is not only charged with process steam but is, in addition, externally heated.

5. The process as claimed in claim 1, wherein process steam is furnished and passed into the autoclave by feed lines, the process steam is saturated with liquid by returning to the process steam the condensate produced in the feed lines and in the heating of the autoclave, supplemented by fresh water.

6. The process as claimed in claim 5, wherein the atmosphere removed by suction from the autoclave is freed from microorganisms and solids by passing the atmosphere through at least two filters having decreasing through-hole size, of which at least the coarsest filter can be flushed by process steam passed opposite to the normal through-flow direction and at least the finest of the filters can be impinged by process steam in the normal through-flow direction.

7. The process as claimed in claim 1, wherein a mist zone is provided and the elimination of the odorous substances is carried out by conducting the gaseous fractions through the mist zone, the mists of which are composed of very fine liquid droplets of an uncontaminated washing liquid produced by ultrasonic spraying jets; then conducting the gaseous fractions through a separating layer, composed of a solid material selected from lava and tuff, in a countercurrent flow to a circulation liquid, and then removing the gases by suction via a demister into the environment, the circulation liquid being circulated and having fresh water serving as a dilution medium for the washing liquid added during circulation.

8. The process as claimed in claim 1, wherein the gaseous fractions in the suction mode are conducted through the mist zone and the separating layer.

9. The process as claimed in claim 1, wherein the odorous substances are eliminated by conducting the exhaust atmosphere over an absorption filter which contains activated charcoal.

10. A process for the disinfection of waste as defined in claim 1, wherein said autoclave is provided as a portable unit.

11. An apparatus for disinfecting waste which apparatus comprises a mobile, jacketed autoclave having process steam connections to the autoclave interior and to the jacket space and at least one interior exhaust connection with an exhaust line arranged at an upper region of the autoclave and a jacket space condensate discharge connection arranged at the lowest point of the jacket space; and a power unit comprising: a control unit, at least two solids filters arranged in series in the exhaust line from the autoclave, at least one condenser for the exhausted atmosphere from the interior at least one liquid separator connected to receive atmosphere from the condenser, at least one vacuum pump connected to receive gaseous material from the at least one liquid separator, at least one unit connected to and receiving and deodorizing exhaust air from the vacuum pump, and a waste water line which drains the liquid from the filters and said at least one liquid separators into waste water.

12. The apparatus as claimed in claim 11, wherein at least two liquid separators are present, to which the flow from the condenser can be directed as desired.

13. The apparatus as claimed in claim 11, wherein at least two vacuum pumps, connected in parallel, are present.

14. The apparatus as claimed in claim 11, wherein the unit for deodorizing the exhaust air from the vacuum pump is a gas scrubber.

15. The apparatus as claimed in claim 14, wherein said gas scrubber has a top end and a bottom end and is essentially composed of regions arranged vertically, one above the other, through which regions the gases are passed from bottom to top, a suction pump is provided and disposed downstream of the gas scrubber in the direction of gas flow, and a circulation liquid is provided and circulated through the gas scrubber essentially counter-current to the gas flow from top to bottom, the gas scrubber having in its bottom region an accumulation of circulation liquid in a bath, the gas to be purified being introduced into a lower region above the bottom region and a very fine mist being produced by ultrasonic spraying jets from uncontaminated washing liquid, the air contents being washed out in a separating layer, arranged above said lower region composed of a solid consisting of at least one material selected from a group of materials consisting of lava and tuff, which is sprayed from above by means of a spraying device with circulating liquid, the liquid fractions of the discharged gases passing through a demisting layer arranged above said spraying the spraying device being taken from the accumulation of circulating liquid at the bottom of the scrubber.

16. The apparatus as claimed in claim 15, wherein an external buffer store means for said washing liquid is provided, in the path of circulation of the washing liquid, external to the gas scrubber, which said buffer store means is equipped with a vent orifice and a fresh water feed.

17. The apparatus as claimed in claim 11, wherein said at least one liquid separator is a cyclone separator.

18. The apparatus as claimed in claim 11, wherein the autoclave has a second interior exhaust connection at the lowest point of the autoclave interior.

19. The apparatus as claimed in claim 18 wherein the discharge connection from the lowest point of the autoclave interior opens into the exhaust connection from the upper region of the autoclave interior, downstream of said filters and upstream of said condenser.

20. The apparatus as claimed in claim 11, further comprising: a condensate receiver for receiving the condensate from said process steam feed lines and from the autoclave jacket space, and a return line and a pump for returning the condensate from the condensate receiver to the process steam feed, and a fresh water connection to the condensate receiver.

21. The apparatus as claimed in claim 11, where air cooling means is provided for the condenser.

22. The apparatus as claimed in claim 11, wherein said at least one liquid separator is air-cooled.

23. The apparatus as claimed in claim 11, wherein said two filters are arranged in series for the separation of microorganisms and solids, of which two filters the first filter has a pass size of about 1.2 μm and the second filter is a sterile filter which has a pass size of about 0.2 μm.

24. The apparatus as claimed in claim 23, wherein a valve-controlled process steam feed line opens directly into the series connection between the first filter and the second sterile filter.

25. The apparatus as claimed in claim 11, wherein, a heating means is provided for said at least one vacuum pump.

26. The apparatus as claimed in claim 11, wherein a mobile container is provided and contains the power unit.

27. An apparatus as defined in claim 11, wherein said mobile autoclave is portable and selectively separable from said power unit.

28. In a process for the disinfection of waste by a fractional vacuum-steam process with at least one of a plurality of atmospheric pressure steam phases and a final superatmospheric steam phase with an evacuation following any such steam phase in an autoclave, the autoclave having upper and lower regions, including providing a load of waste to be disinfected and an autoclave, loading the waste into the autoclave, introducing steam into the autoclave at atmospheric pressure a plurality of times, evacuating the autoclave after each steam introduction step, and charging the autoclave with saturated steam at superatmospheric pressure during a final steam introduction step and maintaining the steam pressure until the autoclave is disinfected, wherein the improvement comprises: in the evacuation following an atmospheric pressure steam phase, removing by suction the atmosphere from an upper region of the autoclave; filtering, through a filter with a filter sump, microorganisms from the removed atmosphere and condensing a first part of the atmosphere as a first liquid fraction stored in the filter sump, wherein the filter and the filter sump are connected to the autoclave and are subjected to the same conditions as the autoclave; condensing the remaining gaseous parts into a second liquid fraction, eliminating odorous substances from the then remaining gaseous parts and discharging the second liquid fraction having approximately ambient temperature as well as the gaseous fraction to the environment; in the evacuation following a superatmospheric pressure steam phase, eliminating, from the lower region of the autoclave, the condensate, including microorganisms, which is collected there and feeding such condensate to waste water at approximately ambient temperature, and then removing the atmosphere in the autoclave by suction, from one of the lower region and upper region of the autoclave and eliminating from the atmosphere, so removed, the odorous substances prior to discharge of the atmosphere, including microorganisms therein, into the environment.

29. The process as claimed in claim 28, wherein the atmosphere removed by suction from the autoclave is freed from microorganisms and solids by passing the atmosphere through at least two filters having decreasing through-hole size, of which at least the coarsest filter can be flushed by process steam passed opposite to the normal through-flow direction and at least the finest of the filters can be impinged by process steam in the normal through-flow direction.

30. The process as claimed in claim 28, wherein a mist zone is provided and the elimination of the odorous substances is carried out by conducting the gaseous fractions through the mist zone, the mists of which are composed of very fine liquid droplets of an uncontaminated washing liquid produced by ultrasonic spraying jets then conducting the gaseous fractions through a separating layer, composed of a solid selected from material including lava and tuff having substantial surface area, in a countercurrent flow to a circulation liquid, and then removing the gases by suction via a demister, known per se, into the environment, the circulation liquid being circulated and having fresh water serving as a dilution medium for the washing liquid added during circulation.

* * * * *